United States Patent [19]

Friel

[11] Patent Number: 5,061,279
[45] Date of Patent: Oct. 29, 1991

[54] PHOTOCHROMIC DILATING PUPIL FOR OCULAR PROSTHETICS

[76] Inventor: Timothy P. Friel, 172 Westway Rd., #101, Greenbelt, Md. 20770

[21] Appl. No.: 613,145

[22] Filed: Nov. 15, 1990

[51] Int. Cl.$^5$ .............................................. A61F 2/14
[52] U.S. Cl. ......................................... 623/4; 623/5
[58] Field of Search ................. 623/4, 5; 446/14, 389, 446/392; 351/162

[56] References Cited

U.S. PATENT DOCUMENTS 4,272,910  6/1981  Danz .................................... 446/389
4,332,039  6/1982  LaFuente ............................ 446/389

Primary Examiner—Randy Citrin Shay

[57] ABSTRACT

The intent of this invention is to allow for a simulation of natural human pupil dilation in an ocular prosthetic. This will be achieved through the use of photochromic pigments that will change the density of their color in response to differing wavelengths of light from clear to opaque. These pigments would separate two or more pupil disks of differing diameter, and by increasing their density of color in response to different wavelengths of light would opaque successively smaller pupil disks, and give the impression of the contraction of the natural eye's pupil. Upon removal from the source of that wavelength of light the pigment would return to its transparent resting state and reveal the underlying pupil disk simulating a dilated natural pupil.

3 Claims, 1 Drawing Sheet

PHOTOCHROMIC DILATING PUPIL FOR OCULAR PROSTHETICS

BRIEF SUMMARY OF THE INVENTION

It is the object of the invention to provide and improved ocular prosthesis that simulates the natural dilation of the human eye in response to differing light conditions.

A specific object of the invention is to achieve this simulated dilation of the pupil through the use of photochromic materials.

Another specific object of the invention is that the prosthesis be completely self contained.

A further specific object is that it require no external power source or input other than that of the light in the surrounding environment.

The foregoing objects and other features of novelty are achieved by incorporating within the iris and anterior segment of the eye several pupils of decreasing diameter separated by layers of material containing photochromic pigments dye, or film.

BRIEF DESCRIPTION OF DRAWINGS:

FIG. 3 is a view of a complete ocular prosthesis and the relation of the componets of the iris in accordance with the

DETAILED DESCRIPTION

Ocular prosthetics in accordance with the invention are shaped like other ocular prosthetics. They have a impression fit posterior surface which corresponds to the back of the anophthalmic socket and as anterior surface curved in such a manner as to give a proper palpebral opening.

Figure 1:
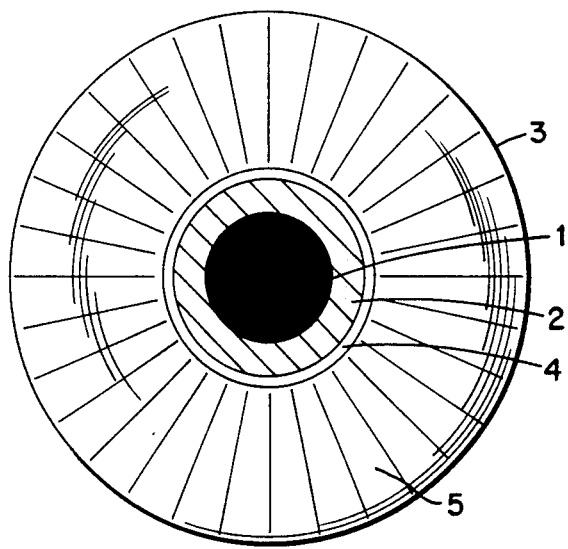
FIG. 1 is front view of the iris in accordance with the invention.

FIG. 1 is a front view of the iris in such a prosthesis. The iris 3 consists of a colored stroma portion 5, a maximum dilation pupil 2, a photochromic layer consisting of photochromic dye, film, or pigment, used to opaque the larger diameter pupil under increased light conditions 4, and a minimum dilation pupil 1.

Figure 2:
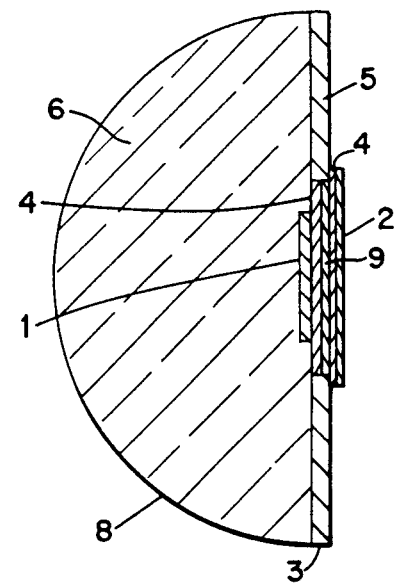
FIG. 2 is a side view of the anterior segment of the eye in accordance with the invention.

FIG. 2 is a side view of the anterior segment in such a prosthesis. The anterior segment 8 consists of the clear corneal layer 6, and the iris 3. The iris is composed of the colored stroma 5, the maximum dilation pupil 2, the photochromic layer 4 including multiple layers of increasing diameter photochromic layers with the diameters of the layers increasing sequentially from the minimum dilation layer to the maximum dilation layer, the intermediate diameter pupil 9, and the minimum diameter pupil 1.

Figure 3:
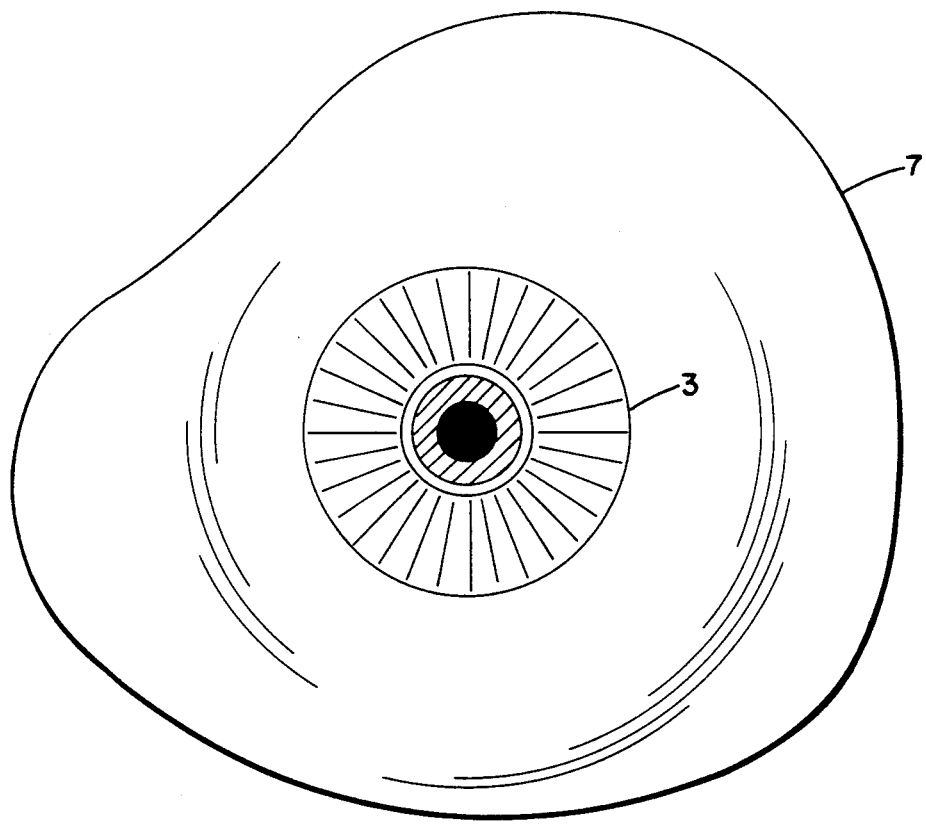

FIG. 3 is a front view of a complete ocular prosthesis 7, and the relation of the components of the iris 3.

What is claimed is:

1. An ocular prosthesis comprising a body portion having an anterior surface and a posterior surface, including an anterior segment received on said anterior surface, said anterior segment comprising an iris coloration layer, a maximum dilation pupil received within an opening in said iris coloration layer, photochromic layer means overlying said maximum dilation pupil for selectively becoming opaque or transparent in response to light wavelengths, thereby determining whether or not the maximum dilation pupil can be seen, a minimum dilation pupil overlying said photochromic layer means, and a clear anterior chamber overlying the iris coloration layer, the maximum dilation pupil, the photochromic layer means and the minimum dilation pupil.

2. The ocular prosthesis of claim 1 wherein the photochromic layer means is a photochromic pigment, dye, or film.

3. The ocular prosthesis of claim 1 further including multiple layers of increasing diameter pupils and photochromic layers with the diameters of the layers increasing sequentially from the minimum dilation layer to the maximum dilation layer.

* * * * *